(12) United States Patent
Ross et al.

(10) Patent No.: US 12,193,665 B2
(45) Date of Patent: Jan. 14, 2025

(54) FIRING LIMIT FEATURE FOR POWERED SURGICAL STAPLER

(71) Applicant: Cilag GmbH International, Zug (CH)

(72) Inventors: Nicholas J. Ross, Franklin, OH (US);
Joseph D. Paulowski, Butler, KY (US);
Shane R. Adams, Lebanon, OH (US);
Matthew D. Cowperthwait, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/490,087

(22) Filed: Oct. 19, 2023

(65) Prior Publication Data

US 2024/0057999 A1 Feb. 22, 2024

Related U.S. Application Data

(63) Continuation of application No. 17/702,054, filed on Mar. 23, 2022, now Pat. No. 11,931,029.

(51) Int. Cl.
*A61B 17/072* (2006.01)
*A61B 34/30* (2016.01)
(Continued)

(52) U.S. Cl.
CPC ...... *A61B 17/072* (2013.01); *A61B 17/07207* (2013.01); *A61B 34/30* (2016.02); *A61B 2017/00022* (2013.01); *A61B 2017/00039* (2013.01); *A61B 2017/00119* (2013.01); *A61B 2017/00221* (2013.01);
(Continued)

(58) Field of Classification Search
CPC ............... A61B 17/068; A61B 17/072; A61B 17/07207; A61B 17/115; A61B 17/32; A61B 17/00234; A61B 2017/00017; A61B 2017/00022; A61B 2017/07214; A61B 2017/2927; A61B 2017/2943; A61B 34/25; A61B 34/30; A61B 34/35; A61B 34/76; A61B 90/98
USPC .............. 227/19, 175.1, 175.2, 176.1, 180.1; 606/1, 139, 219
See application file for complete search history.

(56) References Cited

U.S. PATENT DOCUMENTS 5,562,239 A 10/1996 Boiarski et al.
5,841,284 A 11/1998 Takahashi
(Continued)

FOREIGN PATENT DOCUMENTS

EP 2283780 A2 2/2011

OTHER PUBLICATIONS

International Search Report and Written Opinion dated Jul. 24, 2023 for Application No. PCT/IB2023/052714, 18 pgs.
(Continued)

*Primary Examiner* — Scott A Smith
(74) *Attorney, Agent, or Firm* — Frost Brown Todd LLP

(57) ABSTRACT

A surgical instrument includes a body, a shaft, a motor, a firing assembly, an end effector, and a control circuit. The motor is activatable to actuate the firing assembly through a firing stroke to staple and sever tissue with the end effector. The control circuit is configured to monitor one or more use metrics of the surgical instrument. Responsive to at least one of the one or more use metrics exceeding a predetermined threshold, the control circuit is further configured to initiate at least one of providing a notification to a user or disabling the firing assembly.

20 Claims, 14 Drawing Sheets

(51) Int. Cl.
  *A61B 17/00* (2006.01)
  *A61B 17/068* (2006.01)
  *A61B 17/29* (2006.01)
  *A61B 34/10* (2016.01)
  *A61B 90/98* (2016.01)

(52) U.S. Cl.
  CPC .......... *A61B 17/00234* (2013.01); *A61B 2017/00398* (2013.01); *A61B 17/068* (2013.01); *A61B 2017/07214* (2013.01); *A61B 2017/07285* (2013.01); *A61B 2017/2927* (2013.01); *A61B 34/10* (2016.02); *A61B 90/98* (2016.02)

(56) References Cited

U.S. PATENT DOCUMENTS

| | | | |
|---|---|---|---|
| 7,404,508 B2 | 7/2008 | Smith et al. | |
| 7,434,715 B2 | 10/2008 | Shelton, IV et al. | |
| 7,644,848 B2 | 1/2010 | Swayze et al. | |
| 7,721,930 B2 | 5/2010 | McKenna et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,840,603 B2 | 9/2014 | Giordano et al. | |
| 9,107,690 B2 | 8/2015 | Bales, Jr. et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 10,092,292 B2 | 10/2018 | Boudreaux et al. | |
| 10,383,629 B2 | 8/2019 | Ross et al. | |
| 10,426,468 B2 | 10/2019 | Contini et al. | |
| 10,687,806 B2 | 6/2020 | Shelton, IV et al. | |
| 10,779,849 B2 | 9/2020 | Shelton, IV et al. | |
| 11,071,554 B2 | 7/2021 | Parfett et al. | |
| 11,278,286 B2 | 3/2022 | Contini et al. | |
| 11,311,342 B2 | 4/2022 | Parihar et al. | |
| 11,576,677 B2 | 2/2023 | Shelton, IV et al. | |
| 11,931,029 B2 * | 3/2024 | Ross | A61B 17/072 |
| 2013/0214025 A1 | 8/2013 | Zemlok et al. | |
| 2016/0256154 A1 * | 9/2016 | Shelton, IV | A61B 17/105 |
| 2016/0310134 A1 * | 10/2016 | Contini | A61B 17/0686 |
| 2017/0207467 A1 * | 7/2017 | Shelton, IV | H01M 6/02 |
| 2018/0360471 A1 * | 12/2018 | Parfett | A61B 17/07207 |
| 2019/0125457 A1 * | 5/2019 | Parihar | A61B 17/0206 |
| 2020/0038021 A1 * | 2/2020 | Contini | A61B 17/0686 |
| 2022/0000478 A1 | 1/2022 | Shelton, IV et al. | |
| 2022/0015761 A1 | 1/2022 | Paulowski et al. | |
| 2023/0301650 A1 | 9/2023 | Ross et al. | |

OTHER PUBLICATIONS

U.S. Appl. No. 17/702,054, filed Mar. 23, 2022, by: Ross et al., titled: "Firing Limit Feature for Powered Surgical Stapler."

\* cited by examiner

FIRING LIMIT FEATURE FOR POWERED SURGICAL STAPLER

PRIORITY

This application is a continuation of U.S. patent application Ser. No. 17/702,054, entitled "Firing Limit Feature for Powered Surgical Stapler," filed Mar. 23, 2022, now U.S. Pat. No. 11,931,029 published as U.S. Pat. Pub. No. 2023/0301650 on Sep. 28, 2023, issued as U.S. Pat. No. 11,931,029 on Mar. 19, 2024, the disclosure of which is incorporated by reference herein, in its entirety.

BACKGROUND

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein in its entirety.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
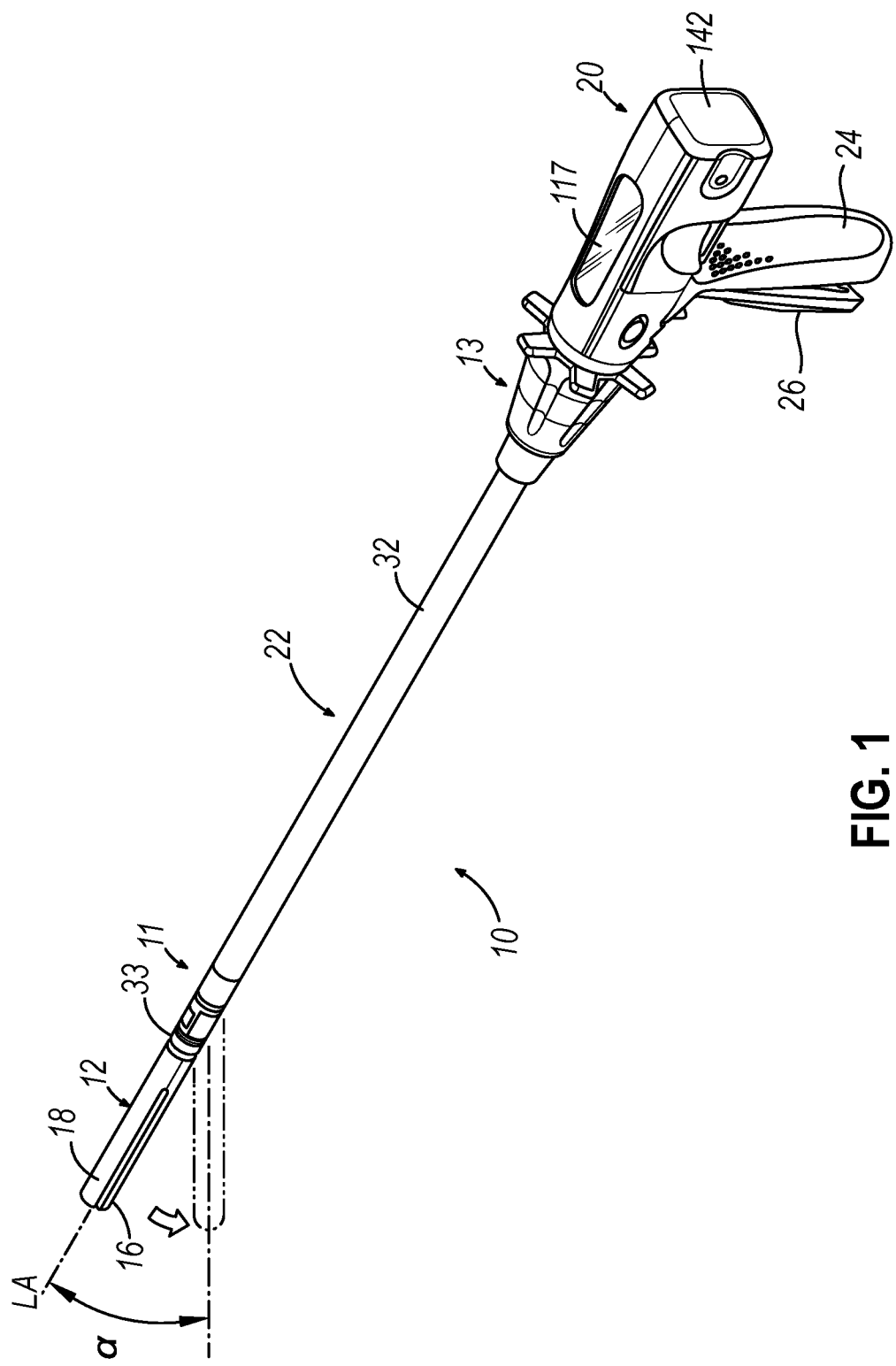
FIG. 1 depicts a perspective view of an exemplary articulating surgical stapling instrument.
Figure 2:
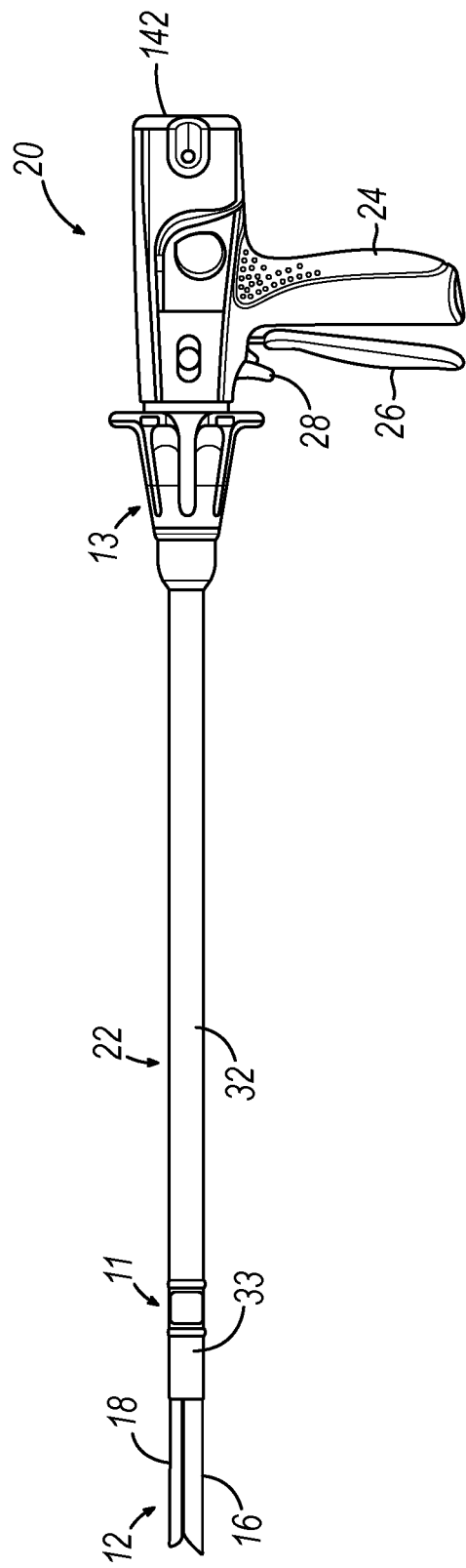
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Illustrative Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint

(11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20), for example via a motor (140) (shown schematically in FIG. 14) housed within handle portion (20), to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
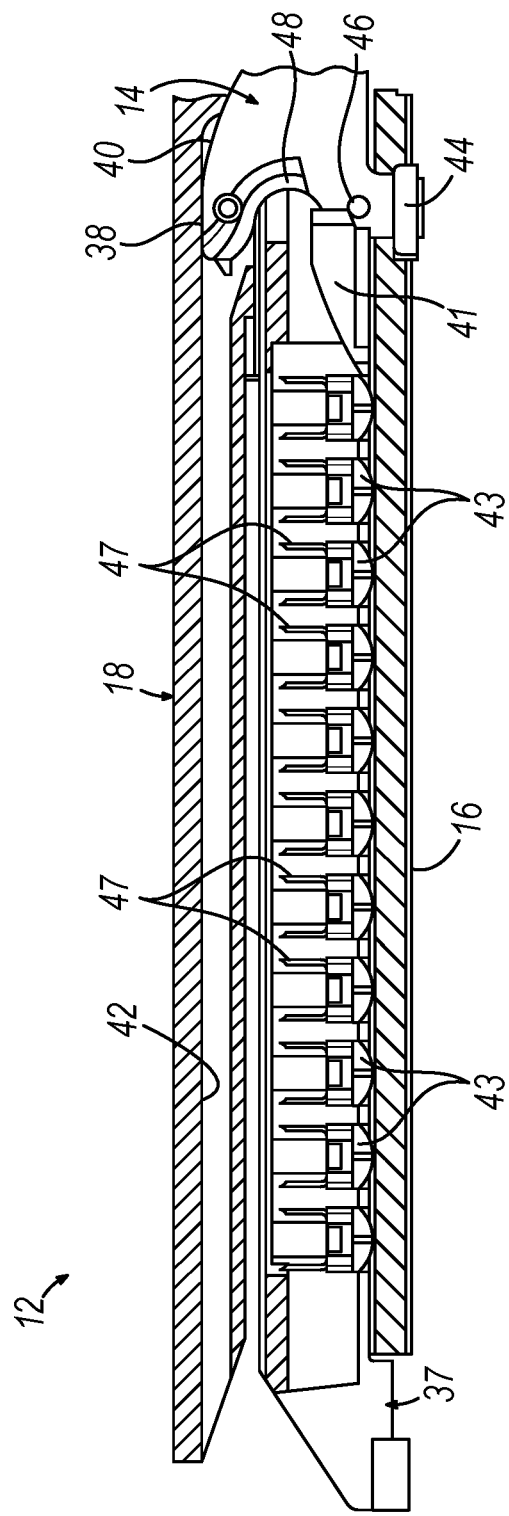
FIG. 4A depicts a side cross-sectional view of the end effector of FIG. 3, taken along line 4-4 of FIG. 3, with a firing beam of the end effector in a proximal position.
Figure 4B:
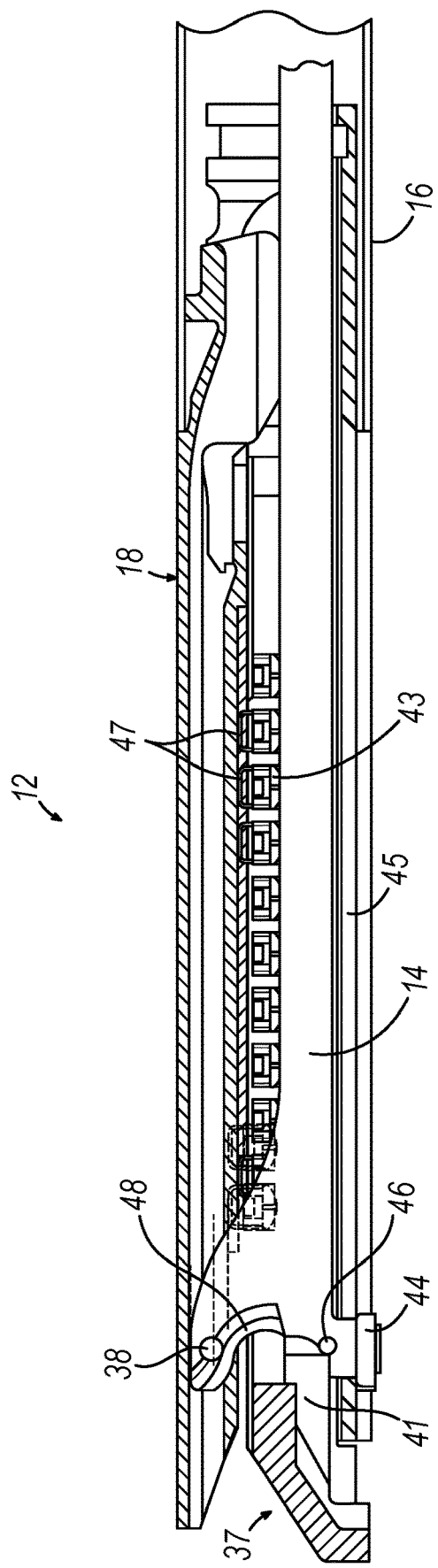
FIG. 4B depicts a side cross-sectional view of the end effector of FIG. 3, taken along line 4-4 of FIG. 3, with the firing beam in a distal position.

As seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
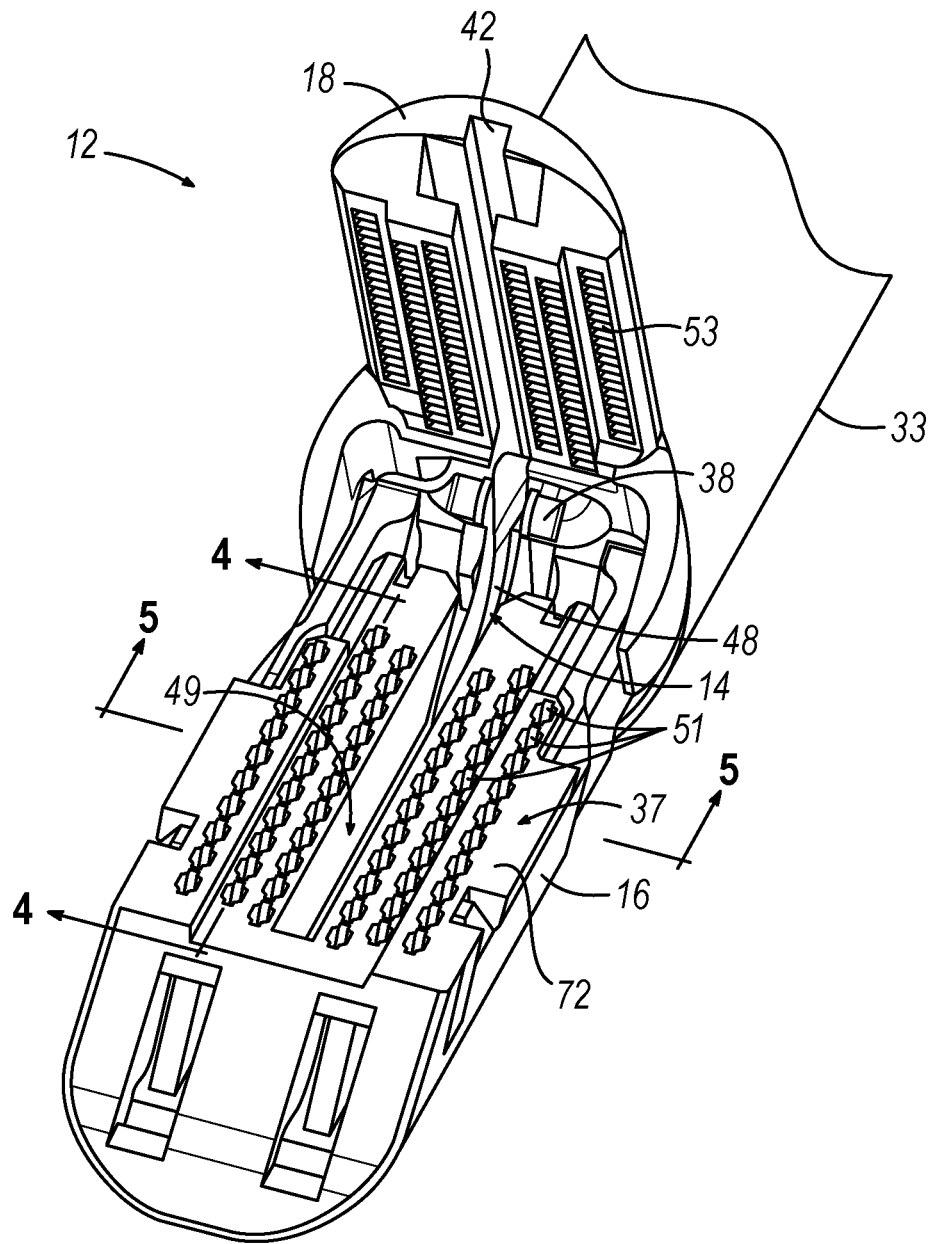
FIG. 3 depicts a perspective view of an opened end effector of the instrument of FIG. 1.
Figure 5:
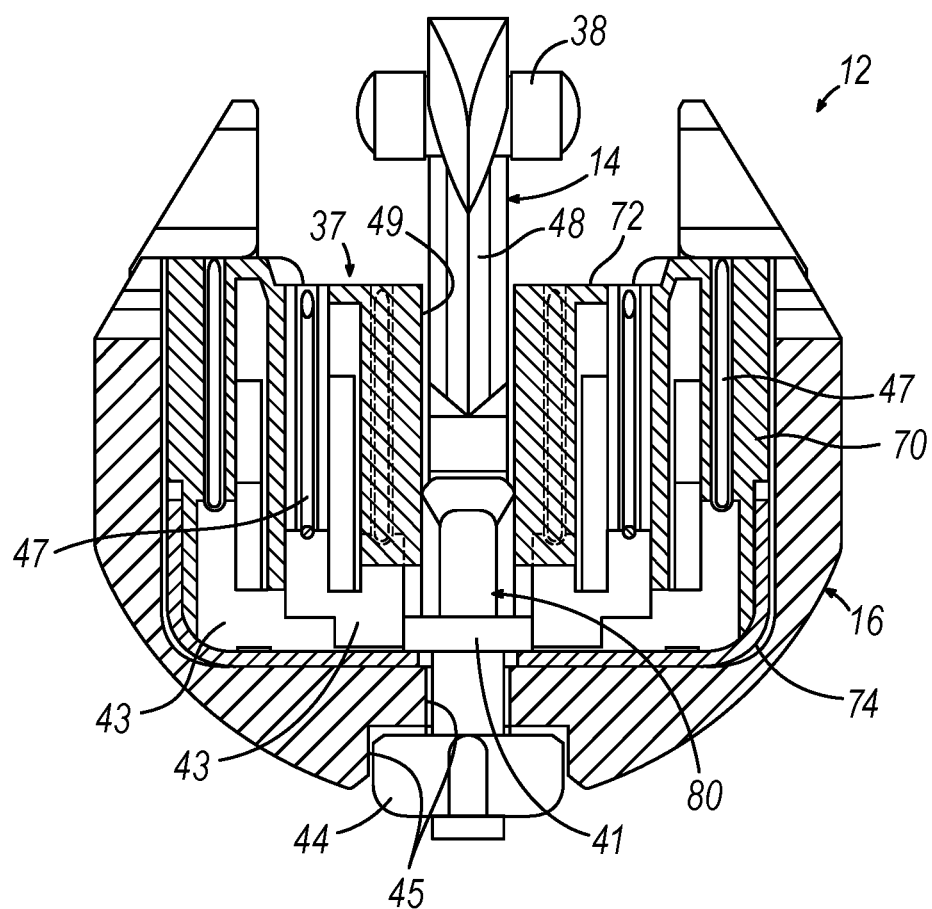
FIG. 5 depicts an end cross-sectional view of the end effector of FIG. 3, taken along line 5-5 of FIG. 3.
Figure 6:
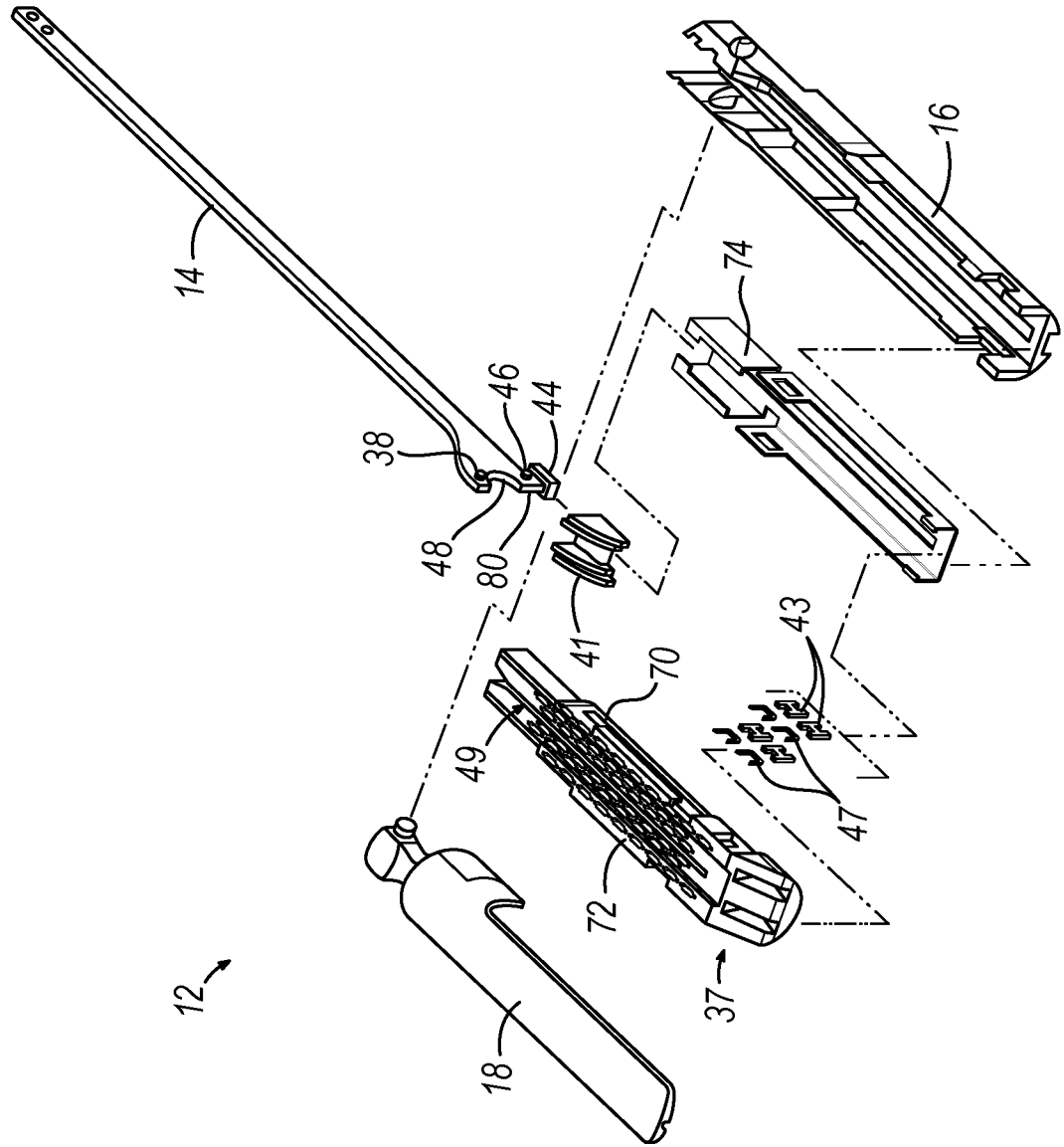
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As seen in FIGS. 5-6, staple cartridge (37) of this example includes a cartridge body (70), which presents an upper deck (72) and is coupled with a lower cartridge tray (74). As seen in FIG. 3, a vertical slot (49) is formed through part of staple cartridge (37). As also seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
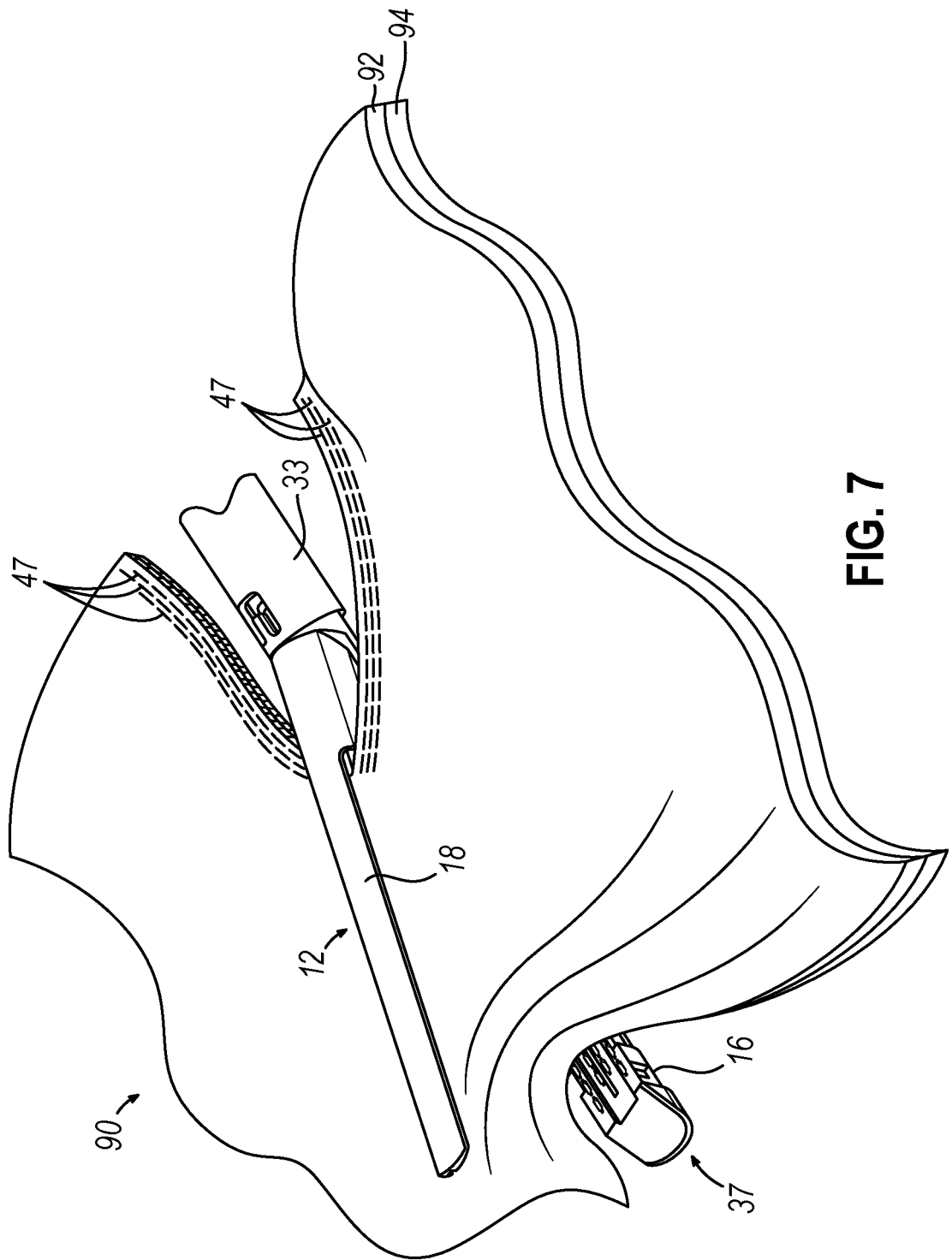
FIG. 7 depicts a perspective view of the end effector of FIG. 3, positioned at tissue and having been actuated once in the tissue.

FIG. 7 shows end effector (12) having been actuated through a single stroke through layers (92, 94) of tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In the present version, instrument (10) further includes an electric motor (140) (shown schematically in FIGS. 8 and 14) housed within handle portion (20) that provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

In motorized versions of instrument (10), instrument (10) may also include a manual return switch, or "bail out switch," (104) (see, FIG. 8) positioned on or within handle portion (20), such as within or under a user-accessible panel or "bail out door" (not shown), the bail out switch (104) being configured to enable the operator to quickly begin retracting firing beam (14) proximally during a firing stroke. In other words, bail out switch (104) may be manually actuated when firing beam (14) has only been partially advanced distally. Bail out switch (104) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein. To access the bail out switch (104), the operator first opens the bailout door (30).

Instrument (10) of the present example further includes a display screen (117) on an exterior of handle portion (20) such that display screen (117) is readily visible to a user. Display screen (117) may be configured to provide a visual indication to the user of one or more statuses of instrument (10), such as a remaining power level of a battery (142) (e.g., a removable battery pack), and/or various other conditions of instrument (10), for example as described in greater detail below.

II. Illustrative Control and Lockout Circuits

A. Overview

As previously described with reference to FIGS. 1-7, various components of a firing assembly of instrument (10) are operable to translate firing beam (14) for stapling and severing clamped tissue via end effector (12). In the present version, a motor (140) is configured to activate to actuate end effector (12) in response to a firing actuation of firing trigger (28), first in a "forward" direction to advance firing beam (14) distally to cut and staple tissue, and next in a "backward" direction to retract firing beam (14) proximally once the cutting and stapling has been completed. Once the two-stage firing stroke is complete (i.e., a stapling operation has concluded and cutting edge (48) and firing beam (14) have been retracted), the motor (140) is configured to deactivate. Further, the motor (140) can be controlled using a firing circuit and/or control algorithm to actuate end effector (12) at one or more predetermined speeds through the firing stroke, thereby providing a predetermined time period for completing the firing stroke. In some examples, the predetermined time period may range from approximately 1 second in duration to approximately 10 seconds in duration. In other examples, the predetermined time period may range from approximately 3 seconds in duration to approximately 7 seconds in duration.

Figure 8:
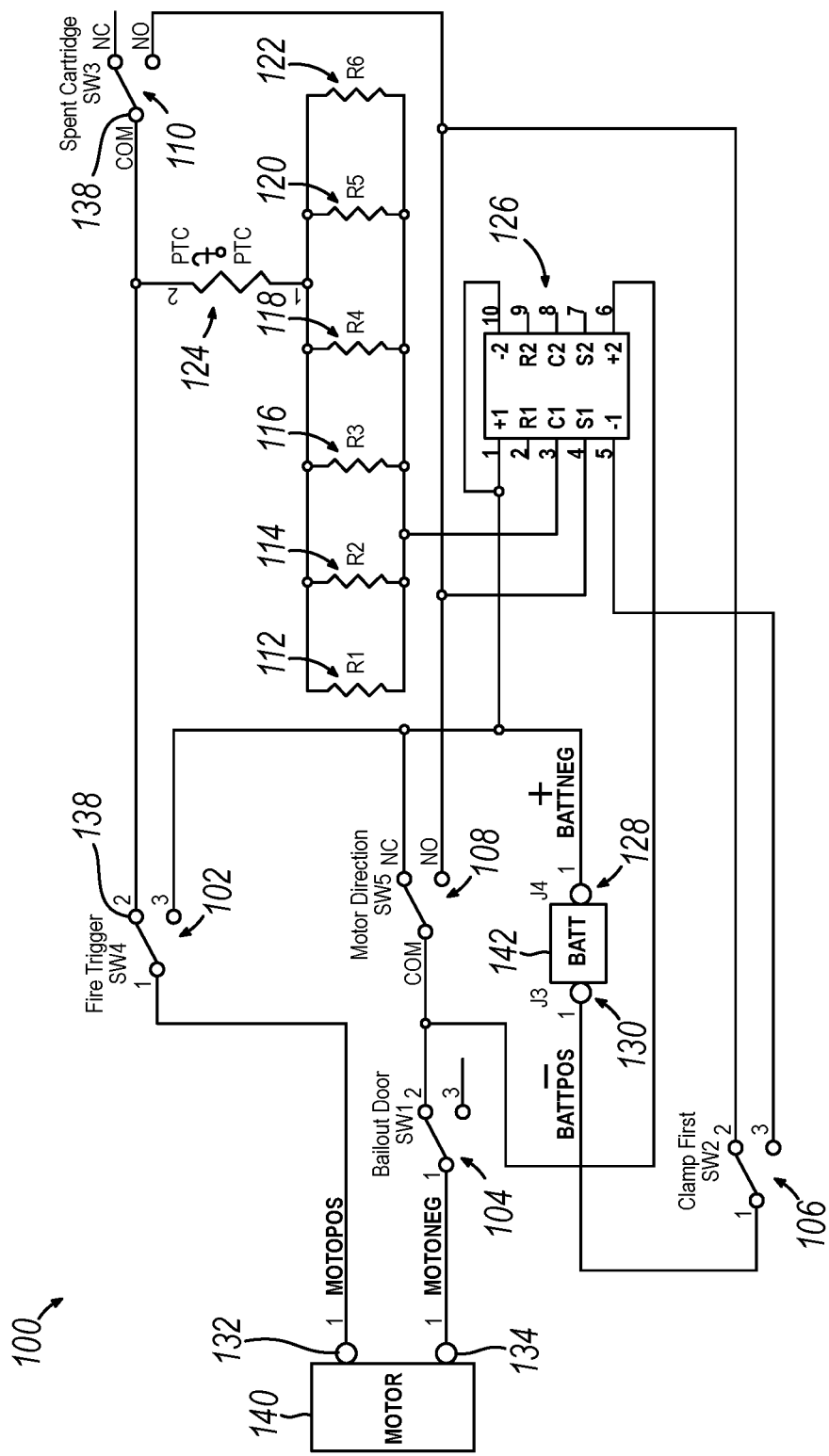
FIG. 8 depicts a schematic view of an exemplary control circuit that may be incorporated into the instrument of FIG. 1.

In the present example, instrument (10) provides motorized control of firing beam (14). FIG. 8 shows an exemplary control circuit (100) that may be incorporated into instrument (10) to provide motorized control of firing beam (14). In particular, FIG. 8 shows an exemplary control circuit (100) that may be used to power electric motor (140) with electric power from battery (142). The motor (140) is operable to translate firing beam (14) longitudinally in a manner as will be described in greater detail below. It should be understood that the entire control circuit (100), including motor (140) and battery (142), may be housed within handle portion (20). By way of example only, motor (140) may be incorporated into instrument (10) in accordance with at least some of the teachings of U.S. Pat. No. 8,453,914, the disclosure of which is incorporated by reference herein in its entirety.

As shown, control circuit (100) of this example includes several switches (102, 104, 106, 108, 110), several resistors (112, 114, 116, 118, 120, 122), a thermistor (124), and a relay (126), these components being configured and operable to selectively couple the positive and negative terminals (128, 130) of battery (142) with the positive and negative terminals (132, 134) of motor (140) to selectively power motor (140).

More specifically, control circuit (100) of the present example includes a fire trigger switch (102), which is configured to be actuated from the "3" position to the "2" position by an actuation of firing trigger (28). Control circuit (100) also includes a bail out switch (104), which is configured to be actuated from the "2" position to the "3" position to effectively disconnect the negative motor terminal (134) upon actuation of bail out switch (104). Control circuit (100) also includes a clamp switch (106), which is configured to be actuated from the "3" position to the "2" position upon a determination that anvil (18) has sufficiently closed to permit a safe and effective firing stroke. Control circuit (100) also includes a motor direction switch (108). Once firing beam (14) reaches a distal-most position (e.g., at the end of a cutting stroke) and cartridge (37) is spent, switches (108, 136) automatically switch from first positions to second positions and relay (126) is latched "open," thereby reversing the polarity of the voltage applied to motor terminals (132, 134). This reverses the direction of rotation of motor (140), it being understood that the operator will have released closure trigger (26) at this stage of operation. Once actuation firing trigger (28) is released and fire trigger switch (102) is actuated back to the "3" position, relay (126) is latched "closed." In some versions, current flows through a reverse direction indicator (e.g., including an optional LED, etc.) to provide a visual indication to the operator that motor (140) rotation has been reversed. Various suitable ways in which switch (108) may be automatically switched to a second position when firing beam (14) reaches a distal-most position will be apparent to those skilled in the art in view of the teachings herein.

In some instances, and as described further herein, control circuit (100) may include a lockout switch (110), which is configured to be closed by default but may be automatically opened in response to a lockout condition. It should be understood that control circuit (100) is opened and thus motor (140) is inoperable when lockout switch (110) is opened in response to detection of a lockout condition. By way of example only, a lockout condition may include one or more of the following: the absence of a cartridge (37) in lower jaw (16), the presence of a spent (e.g., previously fired) cartridge (37) in lower jaw (16), or the presence of an incompatible cartridge in lower jaw (16). In a further instance, a secondary circuit, as discussed herein, may be utilized to detect a lockout condition based on a determination that instrument (10): (i) has been fired too many times, (ii) has a low power level, or (iii) has reached a maximum stress threshold. Various sensors, algorithms, and other features that may be used to detect lockout conditions will be apparent to those skilled in the art in view of the teachings herein.

Instrument (10) may further include a lockout indicator, such as an LED or another visible indicator on display screen (117) operable to provide a visual indication of the status of lockout switch (110). By way of example only, lockout switch (110) and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein. While FIG. 8 shows various switches (102, 104, 106, 108, 110) in certain positions, it should be understood that each switch (102, 104, 106, 108, 110) is independently operable to perform a specific function and is therefore variable depending on the circumstances of operation of instrument (10) in a particular instance.

Control circuit (100) may be further configured in accordance with any one or more of the teachings of U.S. Pat. No. 8,210,411, entitled "Motor-Driven Surgical Instrument," issued Jul. 3, 2012, the disclosure of which is incorporated by reference herein; and U.S. Pub. No. 2022/0015761, entitled "Firing Circuit and Control Algorithm for Surgical Stapler," published Jan. 20, 2022, the disclosure of which is incorporated by reference herein.

B. Illustrative Lockout Circuit Using a Counter

In some instances, instrument (10) may be designed with a limit to the number of times it can be fired safely. More specifically, it may be possible for one or more components of instrument (10) to degrade, break, or otherwise fail if the component is pushed beyond its design limits. Accordingly, it may be desirable to incorporate one or more electrical circuit features into instrument (10) that may be configured to track a usage metric of instrument (10), such as quantity of firings, a stress of firing assembly components, and/or a remaining power of battery (142), and manipulate the power provided to motor (140) to deactivate the motor (140), and thereby disable or "lockout" the firing assembly, in response to detecting that instrument (10) has reached a predetermined maximum allowable use threshold, thereby reducing the potential for component failure and resulting malformation of staples in patient tissue.

Figure 9:
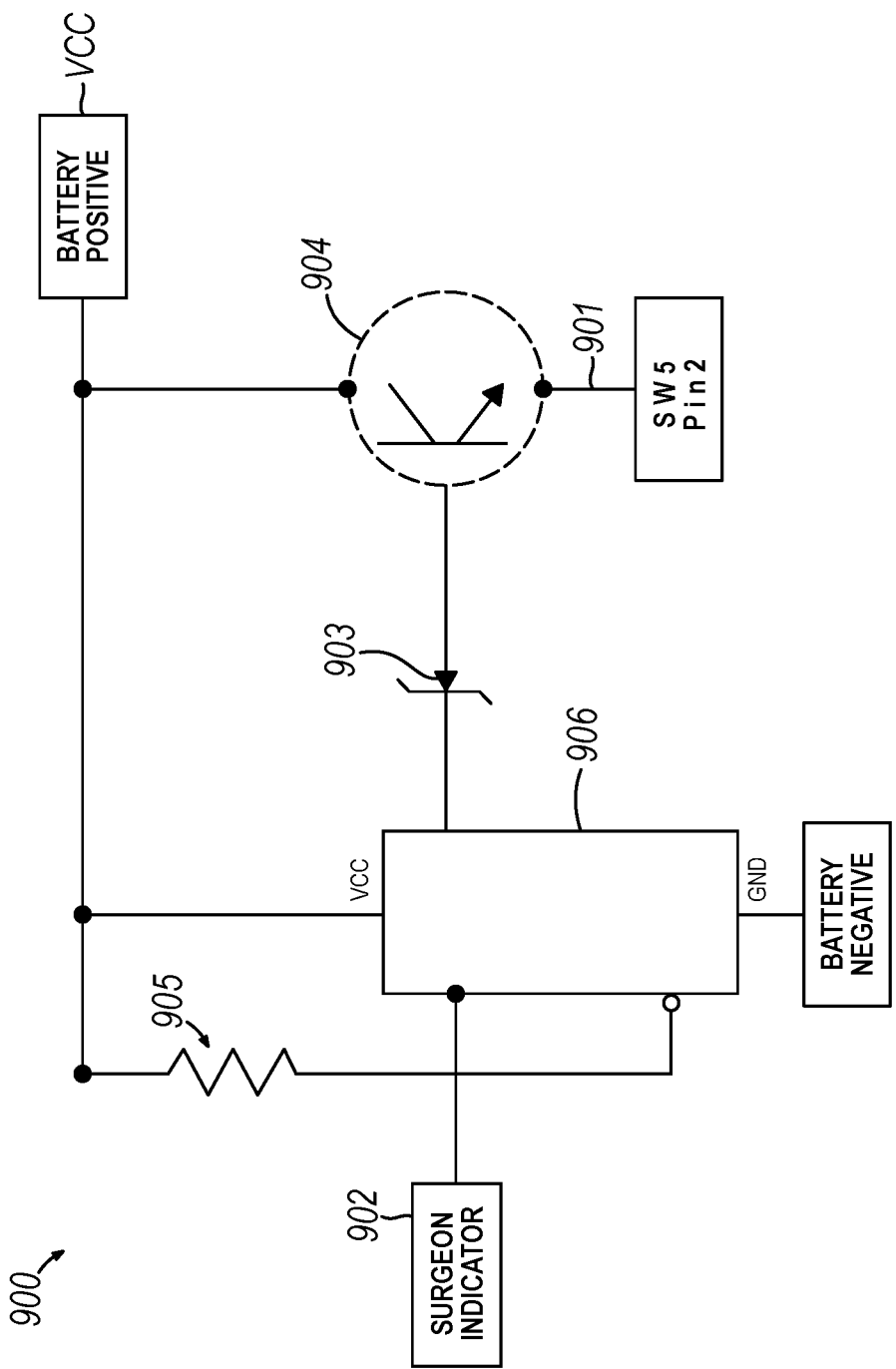
FIG. 9 depicts a first exemplary lockout circuit that may be incorporated into the control circuit of FIG. 8.

As discussed above, battery (142) of instrument (10) is configured to power motor (140) through control circuit (100) to "fire" (i.e., actuate) end effector (12) to thereby staple and cut tissue compressed by end effector (12). Referring now to FIG. 9, instrument (10) may further include a second control circuit in the form of a lockout circuit (900) that is operatively connected to control circuit (100). As described in greater detail below in connection with FIGS. 10-13, lockout circuit (900) is operable to monitor one or more conditions of instrument (10) relative to one or more corresponding maximum allowable use thresholds. In response to determining that a threshold has been reached, lockout circuit (900) may then act upon control circuit (100) to disrupt the electrical connection between motor (140) and battery (142) to prevent additional firings of instrument (10), thus placing instrument (10) in a "lockout" state. Additionally, or alternatively, lockout circuit (900) may instruct that an indication (e.g., visible, audible, and/or tactile) be provided to the user that the threshold has been reached such that no further firings should be performed.

By way of non-limiting example, and as shown, the lockout circuit (900) may connect to the second pin (i.e., Pin2) of switch 5 (i.e., SW5) (901). However, it should be understood, that the output (901) of the lockout circuit (900) may be connected to various other switches, such as, for example, switch 3 (i.e., SW3) shown at (136) of FIG. 8. In a further instance, one or more additional switches may be added to the control circuit (100), which may then be used to disconnect the battery (142) from the motor (140).

As shown, lockout circuit (900) of this example may include a diode (903), a transistor (904), a resistor (905), and a logic device (906). In the present example, transistor (904) may be a Negative-Positive-Negative (NPN) bipolar junction transistor, by way of specific example, transistor (904) may be a 2N3904 General Purpose Transistor manufactured by ON Semiconductor, Inc. Alternatively, any other suitable kinds of transistors may be used. Diode (903) can be, for example, 1N4148 Small Signal Diodes manufactured by ON Semiconductor, Inc. Alternatively, any other suitable kinds of diodes may be used. Further, the logic device (906) may be in the form of a counter, such as an HD74HC4040 12-stage Binary Counter manufactured by Renesas Electronics Corporation, shown as element (1000) in FIG. 10. Alternatively, any other suitable kinds of counters may be used.

As described above, the surgical instrument (10) may have a handle portion (20) that includes a firing trigger (28), which is operatively coupled with motor (140) and battery (142) via control circuit (100) such that power is directed from battery (142) to motor (140) in response to actuation of firing trigger (28) by a user to thereby acuate the firing assembly of instrument (10) and "fire" end effector (12) to simultaneously staple and cut patient tissue clamped between jaw (16) and anvil (18).

Figure 11:
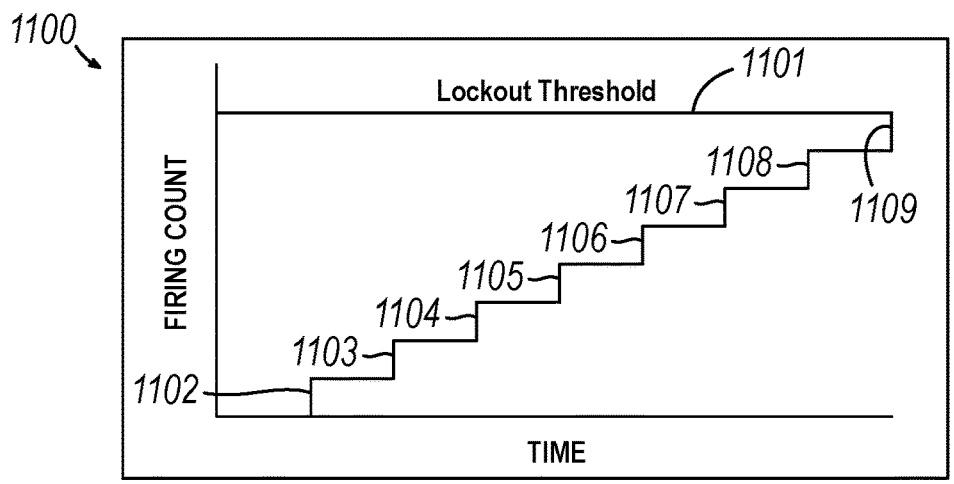
FIG. 11 depicts a graph illustrating a firing count approaching a lockout threshold over time, associated with an exemplary version of the instrument of FIG. 1.

As stated herein, and as shown in FIG. 11 by graph (1100), a predetermined lockout threshold (1101) may be established for a surgical instrument (10) based on a maximum quantity of allowable firings of instrument (10). It should be understood that the lockout threshold (1101) may be different for different devices. Thus, although the illustrative example of FIG. 11 only shows eight (8) distinct firings (i.e., 1102, 1103, 1104, 1105, 1106, 1107, 1108, 1109), the threshold (1101) may be based on any suitable number of firings of instrument (10), such as twelve firings. This is because, as discussed above, the lockout threshold (1101) will be based on the known limitations of one or more components of the instrument (10).

Figure 10:
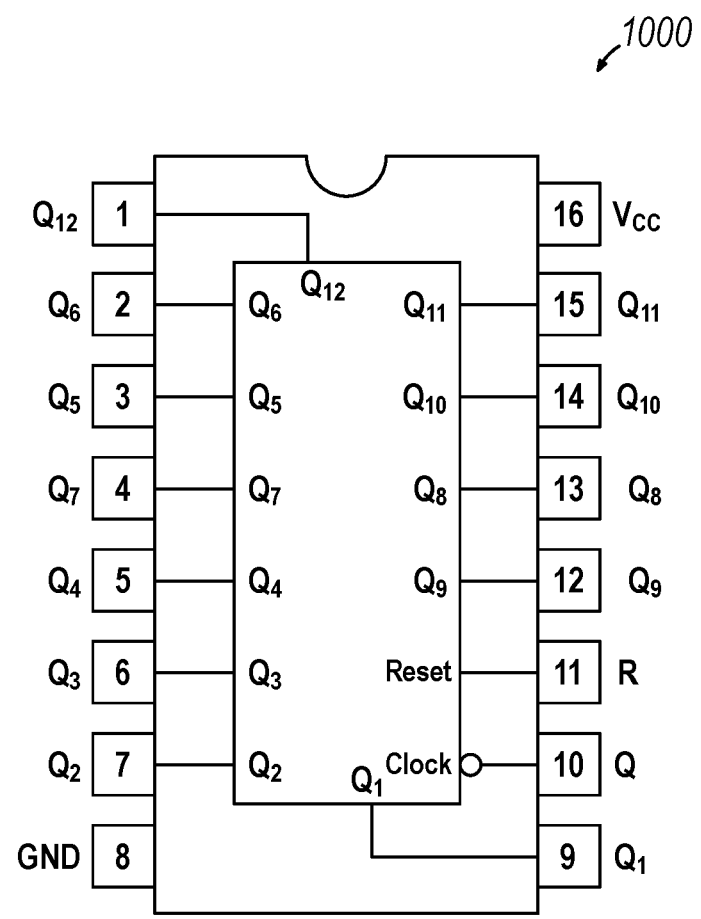
FIG. 10 depicts an example of an electronic counter as used in certain instances.

Accordingly, in some instances, the lockout circuit (900) may utilize a logic device (906) in the form of a counter (e.g., an electronic counter) to maintain a running count of each firing actuation over time, such as shown in FIG. 11. In some instances, and as shown in FIG. 10, the counter may be a 12-stage binary counter. However, it should be understood that any suitable electronic counter may be used. In some instances, the counter may include input features, such as, for example: a reset input that sets count to zero; an enable input that allows or inhibits counting; a direction input that determines whether counts will increment or decrement; a parallel data input that represents a particular count value; a load input that copies parallel input data to the count; and/or a terminal count that indicates that the next clock will cause overflow or underflow. The terminal count may be used to implement counter cascading (i.e., combining two or more counters to create a single, larger counter).

Accordingly, as discussed herein, lockout circuit (900) may be utilized to track and record the total number of times the instrument (10) has be fired, and once the total number meets and/or exceeds the lockout threshold (1101) the firing assembly of instrument (10) is essentially disabled. With respect to the exemplary progression of firings shown in FIG. 11, it should be noted that although each of the distinct firing actuations (i.e., 1102, 1103, 1104, 1105, 1106, 1107, 1108, 1109) appears to have a similar amount of time in between each other, in practice the time intervals between successive firing actuations may be vastly different and FIG. 11 is only shown as an illustrative example.

In some instances, as shown in FIG. 1, the instrument (10) may include a visual indicator, such as, for example, a color changing LED, a numerical display, a gradient display, or the like, which may be provided integrally with or separately from display screen (117), and which is operatively connected to the lockout circuit (900) and displays a useability factor associated with the use of the instrument (10). More specifically, the visual indicator may be configured to display or otherwise visually indicate a count of the total firing actuations, or alternatively, a display of the remaining firing actuations. Additionally, or alternatively, a color change LED may be used to indicate a general usability of instrument (10) (e.g., green=ready, yellow=ready with one use remaining, red=locked out, etc.). Additionally, or alternatively, a gradient display may be used to show the remaining number of uses (e.g., 100% green, 90% green and 10% red, 20% green and 80% red, 100% red, and the like).

C. Illustrative Lockout Circuit Using a Strain Gauge

In some instances, a maximum allowable use of the instrument (10) may be determined wholly or partially by a maximum allowable stress/strain that certain components of instrument (10) can withstand before failure, while accounting for a suitable factor of safety. For instance, it may be possible for one or more components of the firing assembly of the instrument (10) to degrade, break, or otherwise fail if the firing assembly is stressed beyond its design limits. Accordingly, in another exemplary version of lockout circuit (900), logic device (906) may include one or more stress sensors, such as strain gauges (1401, 1403) (see FIG. 14), coupled to a selected one or more components of the firing assembly of instrument (10).

Figure 14:
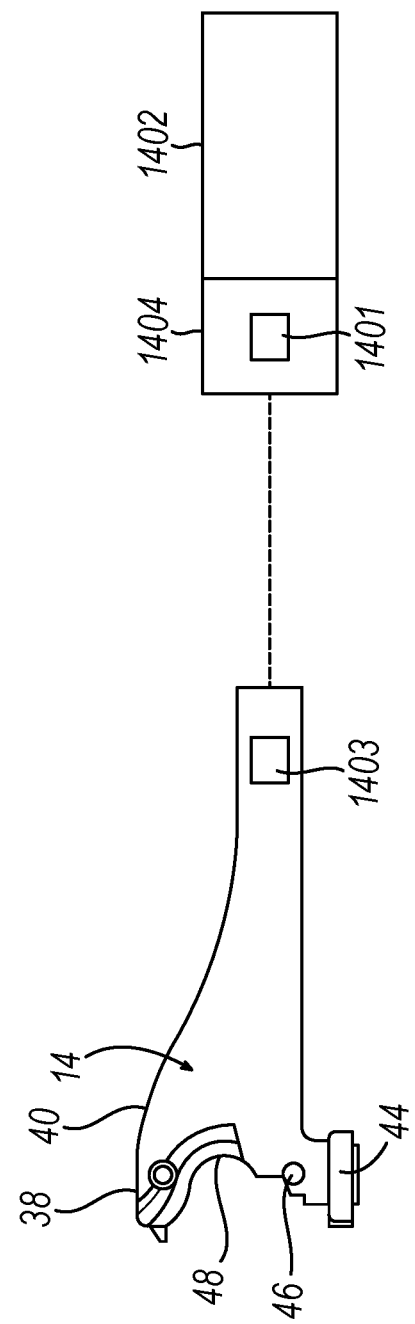
FIG. 14 depicts a schematic view of a portion of a powered firing assembly of the instrument of FIG. 1, showing exemplary strain gauges operatively connected to select components of the powered firing assembly.

FIG. 14 shows an exemplary configuration in which a first strain gauge (1401) is mounted to a motor gear box (1402) coupled with motor (140) to measure forces experienced by motor gear box (1402) during a firing stroke of instrument (10), and a second strain gauge (1403) is mounted to a portion of firing beam (14) to measure forces experienced by firing beam (14) during a firing stroke. It will be appreciated that strain gauges (1401, 1403) of any suitable size and performance may be used. Additionally, while two strain gauges (1401, 1403) are shown in the present example, any suitable quantity and arrangement of strain gauges may be employed in other examples. Each strain gauge (1401, 1403) may be electrically coupled with one or more suitable components integrated into lockout circuit (900) such that lockout circuit (900) is configured to monitor the strain and resulting stress (e.g., where stress is determined as a function of measured strain using known methods) experienced by the corresponding components of the firing assembly of instrument (10).

Figure 12:
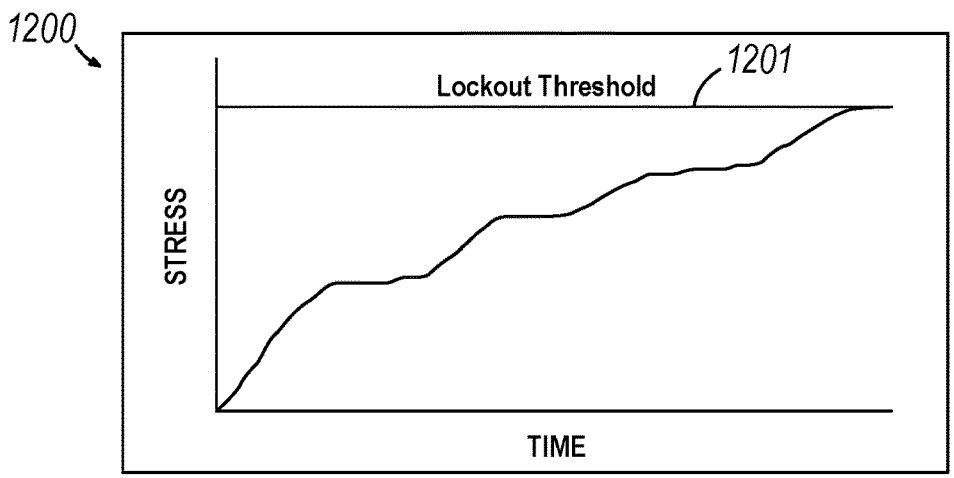
FIG. 12 depicts a graph illustrating a stress level approaching a lockout threshold over time, associated with an exemplary version of the instrument of FIG. 1.

As shown in FIG. 12 by graph (1200), a predetermined lockout threshold (1201) may be established for surgical instrument (10) in terms of a maximum total allowable stress experienced by a selected one or more components of the firing assembly of instrument (10), for example as informed by strain measurements provided by strain gauges (1401, 1403), over the life of instrument (10). As described above in connection with lockout threshold (1101), it should be understood that the lockout threshold (1201) may be different for instruments (10) of different types. As reflected in graph (1200), the lockout circuit (900) may track a cumulative total of stress experienced by the firing assembly components that increases with each successive firing of instrument (10). Upon determining that the lockout threshold (1201) has been met or exceeded, the lockout circuit (900) may affect the control circuit (100) to deactivate the motor (140) to prevent additional firings. Additionally, or in the alternative, the instrument (10) may be configured to provide a visual indication to the user, for example in any one or more of the various manners described above, that the threshold (1201) has been reached. Additionally, as described above, the instrument (10) may be configured to communicate to the user a condition status of the instrument (10) relative to the threshold (1201). Although the illustrative example of FIG. 12 shows a slope that is mostly linear over time, in other examples the slope may be more exponential in nature or have other graphical features not shown in FIG. 12 due to any unique design characteristics of the firing assembly components of the particular instrument (10).

As described above, the lockout circuit (900) may utilize the one or more strain gauges (1401, 1403) mounted to the firing assembly of instrument (10) to monitor stress experienced by the one or more firing assembly components of the instrument (10) to which the one or more strain gauges (1401, 1403) are mounted. In some configurations where multiple strain gauges (1401, 1403) are applied to multiple different components of the firing assembly, the lockout circuit (900) may track a cumulative total stress as informed by the individual strain gauges (1401, 1403) in summation, and then continuously evaluate that cumulative total value relative to a maximum allowable cumulative total stress threshold (1201). In other such configurations, the lockout circuit (900) may track the stress experienced by each firing assembly component individually and either (i) compare the cumulative total stress experienced by that firing assembly component to a respect maximum allowable cumulative total stress threshold for that particular firing assembly component; or (ii) compare the stress experienced by that firing assembly component during each single firing to a respective maximum allowable, single-firing stress threshold for that particular system component. Upon determining that any of the predetermined stress thresholds has been reached, the logic device (906) of lockout circuit (900) could affect the control circuit (100) to deactivate motor (140) and/or provide an indication, in any suitable form, to the user that the threshold has been reached such that no further firings of instrument (10) should be performed.

D. Illustrative Lockout Circuit Using a Power Monitor

In some instances, a maximum allowable use of the instrument (10) may be determined wholly or partially by a minimum allowable remaining power (e.g., as measured by voltage) of the battery (142). In that regard, it will be understood that discharging the battery (142) to an excessively low voltage level may result in the battery (142) being incapable of sufficiently powering the motor (140) through a final portion of a firing stroke, thus risking incompletion of the firing stroke and malformation of staples in patient tissue. Accordingly, in another exemplary version of the lockout circuit (900), the logic device (906) may include or consist of a power monitoring device that is electrically coupled with the battery (142), or alternative power source, and which may be in the form of a voltage meter, for example. It will be appreciated that a power monitoring device of any suitable size or type may be used.

Figure 13:
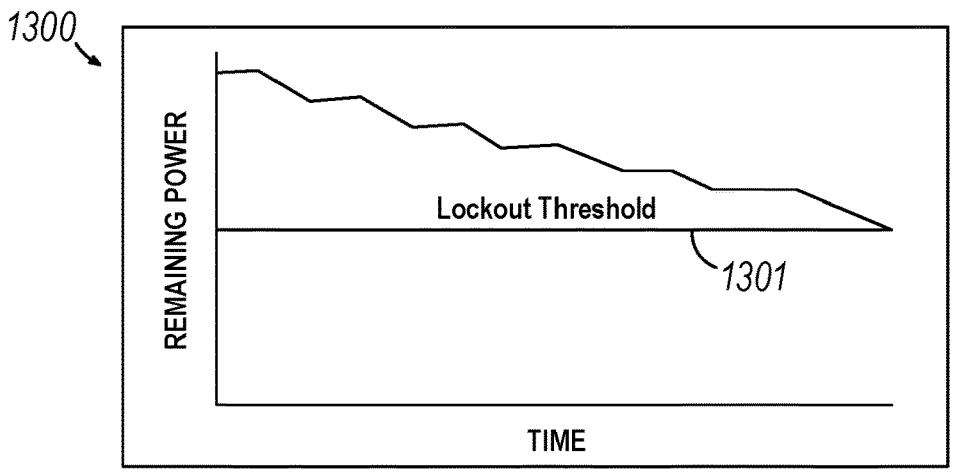
FIG. 13 depicts a graph illustrating a remaining power level approaching a lockout threshold over time, associated with an exemplary version of the instrument of FIG. 1.

As shown in FIG. 13 by graph (1300), a predetermined lockout threshold (1301) may be established for surgical instrument (10) in terms of a minimum allowable remaining power (i.e., voltage) of the battery (142), for example as measured by a power monitoring device that is electrically coupled with the battery (142). In other versions, lockout threshold (1301) may be defined in terms of a maximum allowable power consumed from the battery (142), for example based on a known nominal voltage and/or electrical capacity of the battery (142). It should be understood that the lockout threshold (1301) may be different for different devices, for example to account for differences in characteristics of the corresponding battery (142), such as battery cell type and count (i.e., total nominal voltage), and battery capacity.

Accordingly, in some instances, the lockout circuit (900) may utilize the power monitoring device (e.g., a voltage and/or current reader) to evaluate the remaining battery power of the battery (142) relative to the predetermined lockout threshold (1301) as the battery (142) progressively discharges with each successive firing of the instrument (10). The lockout threshold (1301) may be selected to ensure completion of the final firing stroke driven by the motor (140), including complete formation of the staples in patient tissue, complete cutting of the patient tissue, and complete retraction of the firing beam (14). Upon determining that the lockout threshold (1301) has been met or exceeded, the lockout circuit (900) may affect the control circuit (100) to deactivate the motor (140) to prevent additional firings. Additionally, or in the alternative, the instrument (10) may be configured to provide a visual indication to the user, for example in any one or more of the various manners described above, that the threshold (1201) has been reached.

Additionally, as described above, the instrument (10) may be configured to communicate to the user a condition status of the instrument (10) relative to the threshold (1201), such as a power remaining or a power used of the battery (142). It should be noted that although the slope of the remaining power shown in FIG. 13 appears to be linear, in practice the power usage of each use may vary significantly from one firing to the next, for example as a function of the thickness of patient tissue being fired upon (e.g., where firing on thicker tissue requires the motor (140) to draw a higher current, and thus discharge the battery (142) more substantially during the firing stroke, than when firing on thinner tissue).

Figure 15:
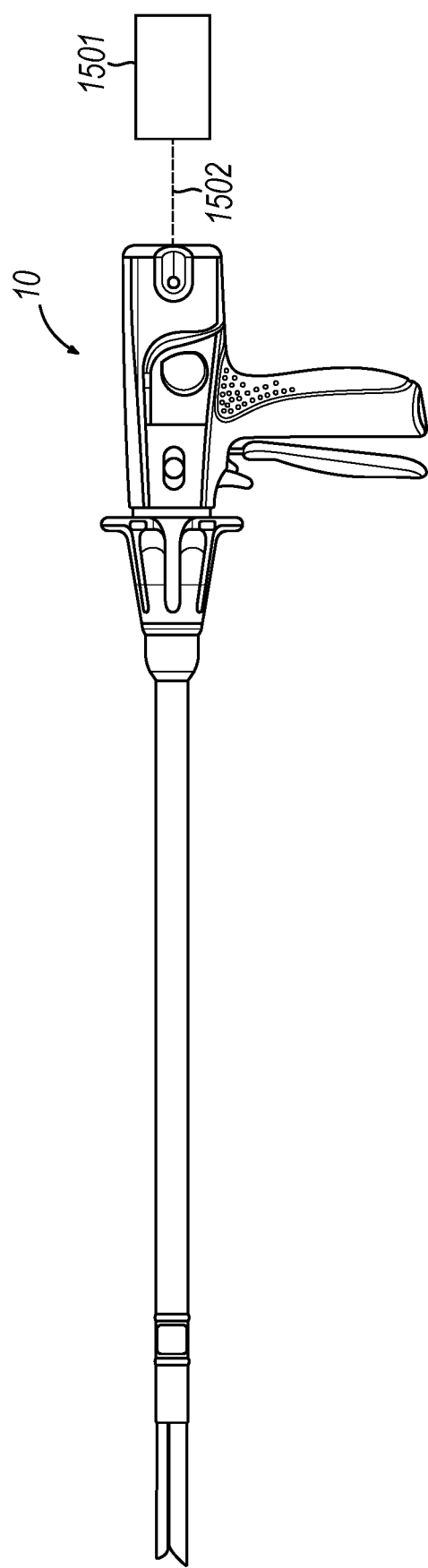
FIG. 15 depicts a schematic view of an exemplary remote device that may be operatively connected to the instrument of FIG. 1.

In some instances, and as shown in FIG. 15, the instrument (10) may include a communication device (e.g., wired or wireless communication module) (not shown) that can communicate (shown via dashed line (1502)) with a remote device (1501), such as an information handling device in the form of a surgical device computer (also referred to as a "hub"). As used herein, a surgical device computer may be any processing device used in a surgical setting or in a setting where the instrument (10) may be used. Surgical device computer (1501) may be operable to communicate with and track one or more conditions of instrument (10). In some instances, surgical device computer (1501) may incorporate or otherwise interface with a surgical navigation system, a surgical planning system, an augmented reality surgical system, or the like. Moreover, the surgical device computer (1501) may be a stationary device (e.g., a desktop computer, server, etc.) or a mobile device (e.g., a laptop, tablet, smartphone, wearable device, etc.).

In such instances where the instrument (10) communicates with a surgical device computer (1501), the lockout circuit (900) would no longer need to perform the monitoring of one or more use metrics of the instrument (10) (e.g., total firings, stress on firing assembly components, and/or remaining battery power) locally, onboard the instrument (10), and thus could be simplified, thereby reducing the cost per unit. In these instances, the remote device (1501) may receive an indication of use (e.g., via a wired/wireless transmission) from the instrument (10) indicating any one or more of (i) completion of a firing, (ii) stress experienced by one or more components of the firing assembly during a firing, and (iii) a remaining power of the battery (142). The remote device (1501) may then track these metrics over the course of multiple firings of the instrument (10) and evaluate them relative to one or more predetermine thresholds (1101, 1201, 1301) of the types described above. Upon determining that one or more such thresholds (1101, 1201, 1301) have been reached or exceeded, the remote device (1501) may instruct the control circuit (100) to deactivate the motor (140) to prevent additional firings. Additionally, or in the alternative, the remote device (1501) may provide directly to the user, or otherwise instruct the instrument (10) to provide to the user, an indication that a threshold (1101, 1201, 1301) has been reached such that no further firings should be performed. Such an indication may be visible, audible, and/or tactile, and may be provided in any of the exemplary manners described above. Additionally, the remote device (1501) may communicate directly to the user, or otherwise instruct the instrument (10) to communicate to the user, a condition status of the instrument (10) relative to any one or more of the predetermined thresholds (1101, 1201, 1301), for instance in any of the exemplary manners described above.

It should be understood that the various additions and alternatives to control circuit (100) described above may be readily used with instrument (10). It should also be understood that, in some instances, the configuration and arrangement of the electrical components of control circuit (100) and lockout circuit (900) may need to be varied in order to complement the configuration and arrangement of the features of instrument (10) described herein. Various suitable ways in which the alternatives to control circuit (100) and lockout circuit (900) described herein may be incorporated into instrument (10) will be apparent to those skilled in the art in view of the teachings herein.

III. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body; (b) a shaft extending distally from the body; (c) a motor configured to couple with a power source; (d) a firing assembly coupled with the motor; (d) an end effector disposed at a distal end of the shaft, wherein the motor is activatable to actuate the firing assembly of the surgical instrument through a firing stroke to staple and sever tissue with the end effector; and (f) a control circuit operatively coupled with the motor and configured to monitor one or more use metrics of the surgical instrument, wherein, responsive to at least one of the one or more use metrics exceeding a predetermined threshold, the control circuit is further configured to initiate at least one of: (i) providing a notification to a user, or (ii) disabling the firing assembly.

Example 2

The surgical instrument of Example 1, wherein the one or more use metrics comprise at least one of a firing stroke count, an applied stress experienced by the firing assembly, or a total remaining power of the power source.

Example 3

The surgical instrument of Examples 1 or 2, wherein the predetermined threshold is determined by a maximum allowable firing stroke count of the surgical instrument, wherein the control circuit comprises a counter configured to monitor a firing stroke count of the surgical instrument.

Example 4

The surgical instrument of Example 3, wherein the counter comprises a binary counter.

Example 5

The surgical instrument of Example 3, wherein the counter is a 12-stage counter.

Example 6

The surgical instrument of Examples 1 or 2, wherein the predetermined threshold is defined by a maximum allowable applied stress experienced by the firing assembly, wherein the control circuit is operatively coupled to at least one strain gauge operatively coupled with the firing assembly, wherein the control circuit is configured to determine an applied stress experienced by the firing assembly based on one or more signals provided by the at least one strain gauge.

Example 7

The surgical instrument of Example 6, wherein the at least one strain gauge is operatively connected to at least one of: the motor, a motor gear box coupled with the motor, or a firing member slidably disposed within the end effector.

Example 8

The surgical instrument of Example 6, wherein the at least one strain gauge comprises a plurality of strain gauges, the plurality of strain gauges being operatively connected to different respective portions of the firing assembly.

Example 9

The surgical instrument of Examples 1 or 2, wherein the predetermined threshold is defined by at least one of a minimum allowable remaining power of the power source or a maximum allowable power consumed from the power source.

Example 10

The surgical instrument of Example 9, wherein the control circuit is operatively coupled to a power monitor configured to determine at least one of a remaining power of the power source or a power consumed from the power source.

Example 11

The surgical instrument of Example 10, wherein the power monitor comprises a voltage meter.

Example 12

The surgical instrument of any of the previous Examples, further comprising a visual indicator configured to display a usability factor associated with the one or more use metrics.

Example 13

The surgical instrument of Example 12, wherein the visual indicator comprises a display configured to display at least one of: a firing stroke count; a difference between a maximum allowable firing stroke count value and a current firing stroke count defined by the most recent firing stroke; a percentage of usability of the surgical instrument remaining; a percentage of usability of the surgical instrument consumed; a percentage of power of the power source remaining; or a percentage of power of the power source consumed.

Example 14

The surgical instrument of any of the previous Examples, wherein the control circuit is operatively coupled to a remote processing device, wherein the remote processing device is configured to monitor the one or more use metrics of the surgical instrument.

Example 15

The surgical instrument of any of the previous Examples, wherein the control circuit is configured to be used in a robotic surgical system.

Example 16

A surgical instrument, comprising: (a) a body; (b) a shaft extending distally from the body; (c) a motor configured to couple with a power source; (d) a firing assembly coupled with the motor; (e) an end effector disposed at a distal end of the shaft, wherein the motor is activatable to actuate the firing assembly of the surgical instrument through a firing stroke to staple and sever tissue with the end effector; and (f) a control circuit operatively coupled with the motor and comprising a counter configured to monitor a firing stroke count of the surgical instrument, wherein, responsive to the firing stroke count exceeding a predetermined threshold, the control circuit is further configured to initiate at least one of: (i) providing a notification to a user, or (ii) disabling the firing assembly.

Example 17

The surgical instrument of Example 16, further comprising a visual indicator configured to display at least one of: a firing stroke count or a difference between a maximum allowable firing stroke count value and a current firing stroke count defined by the most recent firing stroke.

Example 18

The surgical instrument of Examples 16 or 17, wherein the control circuit is operatively coupled to a remote processing device, wherein the remote processing device is configured to monitor the firing stroke count relative to the predetermined threshold.

Example 19

A surgical instrument, comprising: (a) a body; (b) a shaft extending distally from the body; (c) a motor configured to couple with a power source; (d) a firing assembly coupled with the motor; (e) an end effector disposed at a distal end of the shaft, wherein the motor is activatable to actuate the firing system of the surgical instrument through a firing stroke to staple and sever tissue with the end effector; and (f) a control circuit operatively coupled to at least one of: (i) a power monitor configured to enable the control circuit to determine at least one of a remaining power of the power source or a power consumed from the power source, or (ii) a strain gauge configured to enable the control circuit to determine an applied stress experienced by the firing system; wherein, responsive to the applied stress, the remaining power, or the power consumed reaching a predetermined threshold, the control circuit is further configured to initiate at least one of: (i) providing a notification to a user, or (ii) disabling the firing system.

Example 20

The surgical instrument of Example 19, further comprising a visual indicator configured to display at least one of: a percentage of usability of the surgical instrument remaining; a percentage of usability of the surgical instrument consumed; a percentage of power of the power source remaining; or a percentage of power of the power source consumed.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft extending distally from the body;
   (c) a power source having a finite amount of power;
   (d) a motor operatively coupled with the power source;
   (e) a firing assembly operatively coupled with the motor;
   (f) an end effector operatively coupled with the shaft, wherein the motor is activatable to actuate the firing assembly through a firing stroke to staple tissue with the end effector; and
   (g) a control circuit operatively coupled with the power source and the motor and configured to:
      (i) after at least one firing stroke of the surgical instrument, determine that at least one of:
         (A) a remaining power of the power source has reached a minimum allowable remaining power, or
         (B) a power consumed from the power source has reach a maximum allowable power consumed, and
      (ii) after making the determination, initiate an action that comprises at least one of:
         (A) providing a notification to a user, or
         (B) disabling the firing assembly.

2. The surgical instrument of claim 1, wherein the power source includes a battery.

3. The surgical instrument of claim 1, wherein the control circuit is operatively coupled to a power monitor configured to determine at least one of the remaining power of the power source or the power consumed from the power source.

4. The surgical instrument of claim 3, wherein the power monitor comprises a voltage meter.

5. The surgical instrument of claim 4, wherein the power monitor comprises a current meter.

6. The surgical instrument of claim 1, further comprising a visual indicator configured to display a usability factor associated with the power source.

7. The surgical instrument of claim 6, wherein the visual indicator comprises a display configured to display at least one of a percentage of the remaining power or the power consumed.

8. The surgical instrument of claim 6, wherein the visual indicator includes a light emitting diode.

9. The surgical instrument of claim 8, wherein the light emitting diode includes a color changing light emitting diode, wherein the color changing light emitting diode is configured to emit a green color to indicate the power source includes enough power to perform at least two more firing strokes.

10. The surgical instrument of claim 9, wherein the color changing light emitting diode is configured to emit a yellow color to indicate the power source includes enough power to perform only one more firing stroke.

11. The surgical instrument of claim 10, wherein the color changing light emitting diode is configured to emit a red color to indicate the power source no longer has enough power to perform another firing stroke.

12. The surgical instrument of claim 1, further comprising a communication device configured to communicate with a remote device.

13. The surgical instrument of claim 12, wherein the communication device is wireless.

14. The surgical instrument of claim 1, in combination with a surgical device computer configured to communicate with the surgical instrument, wherein the surgical device computer is remotely located relative to the surgical instrument.

15. The surgical instrument of claim 14, wherein the surgical device computer is configured to remotely track one or more conditions of the surgical instrument.

16. A method of operating a surgical instrument, wherein the surgical instrument comprises a power source, a motor operatively coupled with the power source, a firing assembly operatively coupled with the motor, an end effector operatively coupled with the firing assembly and actuatable through a firing stroke to staple tissue, and a control circuit operatively coupled with the power source and the motor, the method comprising:
   activating the motor with the power source to actuate the firing assembly through a firing stroke;
   after completing the firing stroke, determining with the control circuit that at least one of: a remaining power of the power source has reached or exceeded a predetermined threshold of remaining power, or a power consumed from the power source has reached or exceeded a predetermined threshold of power consumed; and
   based on the determination, with the control circuit at least one of: providing a notification to a user, or inhibiting additional firing strokes of the surgical instrument.

17. The method of claim 16, wherein the step of at least one of providing an indication or preventing additional firing strokes includes deactivating the firing assembly of the surgical instrument.

18. The method of claim 17, further comprising displaying at least one of: a percentage of power of the power source remaining or a percentage of power of the power source consumed.

19. The method of claim 18, wherein the surgical instrument further comprises at least one of a light emitting diode or a gradient display.

20. A method of operating a surgical instrument, wherein the surgical instrument comprises a power source, a motor operatively coupled with the power source, a firing assembly operatively coupled with the motor, an end effector operatively coupled with the firing assembly and actuatable through a firing stroke to staple tissue, and a control circuit operatively coupled with the power source and the motor, the method comprising:
   activating the motor with the power source to actuate the firing assembly through a firing stroke;
   after completing the firing stroke, determining with the control circuit that a remaining power of the power source has reached or exceeded a predetermined threshold of remaining power; and based on the determination, with the control circuit inhibiting additional firing strokes of the surgical instrument.

* * * * *